(12) United States Patent
Itou et al.

(10) Patent No.: US 8,764,724 B2
(45) Date of Patent: Jul. 1, 2014

(54) INTRAVASCULAR FOREIGN MATTER SUCTION ASSEMBLY

(75) Inventors: Takenari Itou, Shizuoka (JP); Tetsuya Fukuoka, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 249 days.

(21) Appl. No.: 12/769,066

(22) Filed: Apr. 28, 2010

(65) Prior Publication Data

US 2010/0217237 A1 Aug. 26, 2010

Related U.S. Application Data

(62) Division of application No. 11/232,876, filed on Sep. 23, 2005, now Pat. No. 7,736,355.

(30) Foreign Application Priority Data

Sep. 24, 2004 (JP) ................................ 2004-276291

(51) Int. Cl.
*A61M 31/00* (2006.01)

(52) U.S. Cl.
USPC ...................................................... 604/507

(58) Field of Classification Search
USPC ......... 604/264, 265, 500, 506–508, 510, 523, 604/524, 526
See application file for complete search history.

(56) References Cited

U.S. PATENT DOCUMENTS

| | | |
|---|---|---|
| 5,011,488 A | 4/1991 | Ginsburg |
| 5,226,888 A | 7/1993 | Arney |
| 5,385,562 A | 1/1995 | Adams et al. |
| 5,527,292 A | 6/1996 | Adams et al. |
| 5,569,204 A | 10/1996 | Cramer |
| 5,938,645 A | 8/1999 | Gordon |
| 6,849,068 B1 | 2/2005 | Bagaoisan et al. |
| 2002/0177800 A1 | 11/2002 | Bagaoisan et al. |
| 2003/0050600 A1 | 3/2003 | Ressemann et al. |

FOREIGN PATENT DOCUMENTS

WO  WO 00/69498 A1  11/2000

OTHER PUBLICATIONS

Official Action (Communication Pursuant to Article 96(2) EPC) issued by the European Patent Office in corresponding European Patent Application No. 05 020 435.3, Jul. 25, 2007.

*Primary Examiner* — Aarti B Berdichevsky
(74) *Attorney, Agent, or Firm* — Buchanan Ingersoll Rooney PC

(57) ABSTRACT

An intravascular foreign matter suction assembly is insertable into a blood vessel having a relatively small diameter and exhibits a high suction force. The intravascular foreign matter suction assembly includes a combination of a guiding catheter for being inserted to an ostium of a coronary artery of the aorta and a suction catheter inserted in the lumen of the guiding catheter and extending farther than the distal end of the guiding catheter for removing foreign matter in a blood vessel which exists at a target location in the coronary artery. The suction catheter includes a tubular portion provided on the distal end side and a wire portion provided on the proximal end side of the tubular portion and wherein the wire portion has a distal end embedded in a wall which forms the tubular portion.

20 Claims, 10 Drawing Sheets

FIG. 1A
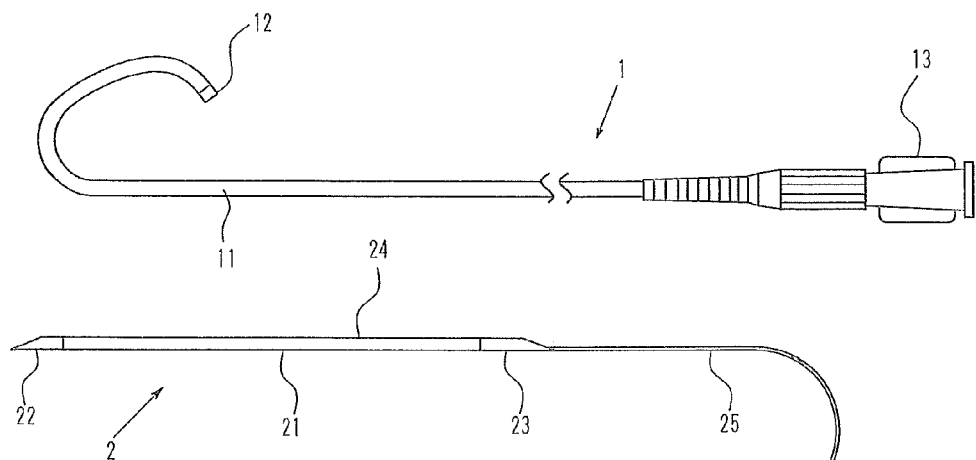
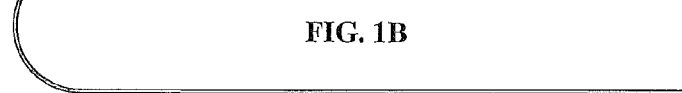
FIG. 1B
FIG. 1C
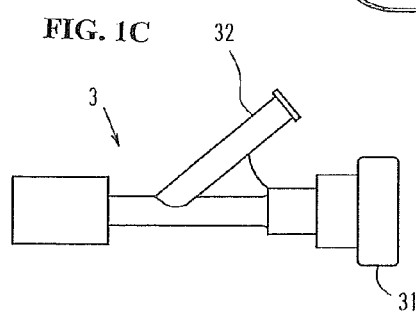
FIG. 1D
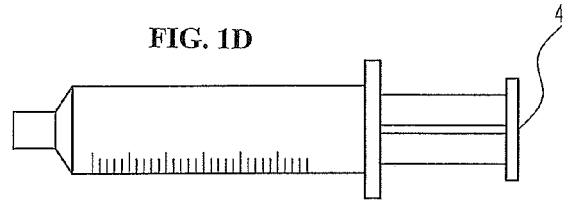
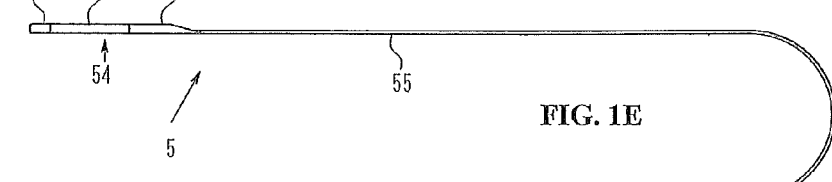
FIG. 1E
FIG. 1F

INTRAVASCULAR FOREIGN MATTER SUCTION ASSEMBLY

CROSS REFERENCE OF RELATED APPLICATIONS

This application a divisional application of U.S. patent application Ser. No. 11/232,876, filed Sep. 23, 2005, now allowed, and claims priority under 35 U.S.C. §119 to Japanese Patent Application No. 2004-276291, filed on Sep. 24, 2004, the entire contents of each of which is incorporated herein by reference.

FIELD OF THE INVENTION

This invention relates to an intravascular foreign manner suction assembly, and method, for sucking, sampling and removing a foreign matter such as a thrombus or an embolus which makes a cause of constriction in a blood vessel.

BACKGROUND OF THE INVENTION

It is known that, if foreign matter such as thrombi or emboli choke a blood vessel such as a coronary artery of the heart, then it obstructs the flow of the blood and causes a serious disorder. One known catheter assembly for sucking such a thrombus as described above is disclosed in U.S. Pat. No. 5,569,204.

The catheter assembly disclosed in U.S. Pat. No. 5,569,204 includes three catheters combined, namely a central catheter, a dilator provided on the inner side of the central catheter, and an outside catheter provided on the outside of the central catheter. After the catheter assembly reaches a target location, the dilator is pulled out, and a thrombus and so forth are sucked and removed through the lumen of the central catheter by a suction device connected to the proximal end of the central catheter. Further, with the catheter assembly disclosed in U.S. Pat. No. 5,569,204, if a thrombus or the like chokes the central catheter, then the central catheter is pulled out, and the pulled out central catheter is washed or a new central catheter is prepared and inserted into the outside catheter, or after the choked central catheter is pulled out, suction is performed using the outside catheter.

The catheter assembly of U.S. Pat. No. 5,569,204 having such a configuration as described above makes use of the lumen of the central catheter or the outside catheter as a suction path for the suction. The inner diameter of the lumen of each of the catheters has a constant dimension from the distal end to the proximal end, and the inner diameter cannot avoid being restricted by the finest portion of the blood vessel into which the catheter assembly is inserted. The finest portion of the blood vessel is usually an extremity position into which the catheter assembly is inserted.

SUMMARY OF THE INVENTION

According to the present invention, an intravascular foreign matter suction assembly for sucking a foreign matter existing in a blood vessel comprises a guiding catheter including a distal end and a proximal end and forming a lumen extending from the distal end to the proximal end configured to be inserted into a blood vessel until a position on proximal side of a target location in the blood vessel is reached. The intravascular foreign matter suction assembly further comprises a suction catheter comprising a tubular portion provided on a distal side of the suction catheter, the tubular portion including a distal tube end and a proximal tube end and a solid wire-like portion provided at the proximal tube end of said tubular portion and having a distal end embedded in a wall which forms said tubular portion. Said suction catheter configured to be inserted in said lumen of said guiding catheter and said tubular portion is configured to project outwardly beyond the distal end of said guiding catheter for removing foreign matter existing at the target location in the blood vessel.

According to a preferred embodiment, the intravascular foreign matter suction assembly is an apparatus for sucking and removing a foreign matter positioned at a deep location in a coronary artery of the heart or the like and includes a guiding catheter for being inserted to a location on proximal side of a target location such as an ostium portion of a coronary artery of the heart in the aorta. The intravascular foreign matter suction assembly further includes a suction catheter extending through the lumen of the guiding catheter into the coronary artery farther than the distal end for sucking thrombi or emboli, and a distal end protective catheter for protecting the wall of the blood vessel from the distal end of the suction catheter.

More preferably, the suction catheter includes a tubular portion provided on the distal side and a solid wire-like portion provided on the proximal side and having a distal end embedded in a wall which forms the tubular portion. Further, the tubular portion of the suction catheter has a soft tip whose distal end is flexible in order to reduce the damage to the blood vessel, and includes a reinforcing member so that, even where it has a small material thickness, it is not kinked and, if the wire-like portion is rotated by a hand, then also the distal end of the suction catheter is rotated. Furthermore, the suction catheter has a hydrophilic lubricative coating layer provided on the surface of an outer side resin layer. Further, the tubular portion of the suction catheter is shorter than the guiding catheter, and the total length of the tubular portion and the wire-like portion is greater than that of the guiding catheter.

The invention also relates to a method of sucking foreign matter from a blood vessel which comprises the steps of:

A) inserting into a blood vessel a guiding catheter until a distal side of the guiding catheter reaches a proximal side of a target location;

B) inserting into a lumen of the guiding catheter a suction catheter comprising a tubular portion and a solid wire portion extending from a proximal side of the tubular portion, wherein a distal side of the tubular portion projects forwardly beyond the distal side of the guiding catheter, and a proximal side of the tubular portion is disposed inside of the guiding catheter; and C) applying suction to the guiding catheter which is transmitted to the tubular portion for sucking the foreign matter into the distal side of the tubular portion.

BRIEF DESCRIPTION OF THE DRAWINGS

The objects and advantages of the invention will become apparent from the following detailed description of a preferred embodiment thereof in connection with the accompanying drawing in which like numerals designate like elements, and in which:

FIGS. 1A-1F are views showing several devices which comprise an intravascular foreign matter suction assembly of the present invention is used; wherein FIG. 1A is a side view of a guiding catheter, FIG. 1B is a side view of a suction catheter; FIG. 1C is a side view of a Y-shaped connector; FIG. 1D is a side view of a suction syringe; FIG. 1E is a side view of a protective catheter; and FIG. 1F is a side view of a guide wire;

FIGS. 9A, 9B are views illustrating a manner of a comparative experiment, wherein FIG. 9A is a schematic view of an example according to the present invention, and FIG. 9B is a schematic view of a comparative example.

DETAILED DESCRIPTION OF THE PREFERRED EMBODIMENTS

Figure 2:
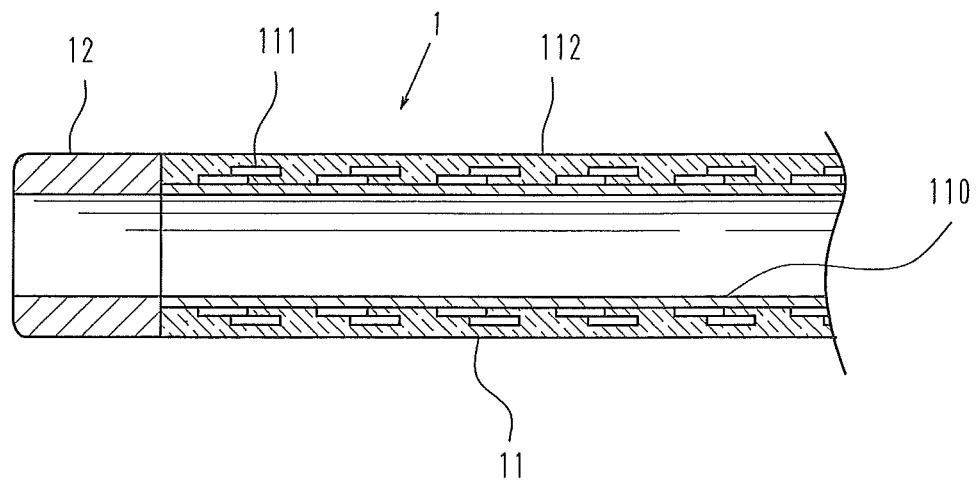
FIG. 2 is a view showing a cross section of a distal end portion of a guiding catheter 1.

FIG. 1 is a view showing several devices used when an intravascular foreign matter suction assembly according to an embodiment of the present invention is used.

Referring to FIGS. 1A-1F, reference numeral 1 denotes a guiding catheter (see FIG. 1A); 2 denotes a suction catheter (see FIG. 1B); 3 denotes a Y-shaped connector serving as a branching connector (see FIG. 1C); 4 denotes a syringe serving as a negative pressure generating device (see FIG. 1D); 5 denotes a distal end protective catheter (see FIG. 1E); and 6 denotes a guide wire (see FIG. 1F).

FIG. 2 shows a sectional view of a distal end portion of the guiding catheter 1 of FIG. 1A. The guiding catheter 1 includes a body portion 11 which in turn includes an inner layer 110 made of a resin material having a sliding property such as a fluorocarbon resin represented by PTFE, a reinforcing layer 111 made of a metal wire made of stainless steel or the like, and an outer layer 112 for covering the reinforcing layer 111, a flexible distal tip 12, and a connector 13 provided at the proximal end of the body portion 11. The body portion 11 forms a tubular wall which defines a lumen. In the flexible distal tip 12, filler such as tungsten, bismuth oxide or barium sulfate which are X-ray contrast agents is mixed by 50 to 70 wt %, and therefore, the flexible distal tip 12 functions as an X-ray contrast marker (radiopaque marker). Therefore, the operator can confirm the position of the distal end portion of the guiding catheter 1 in the body of the patient on an X-ray image.

Figure 3:
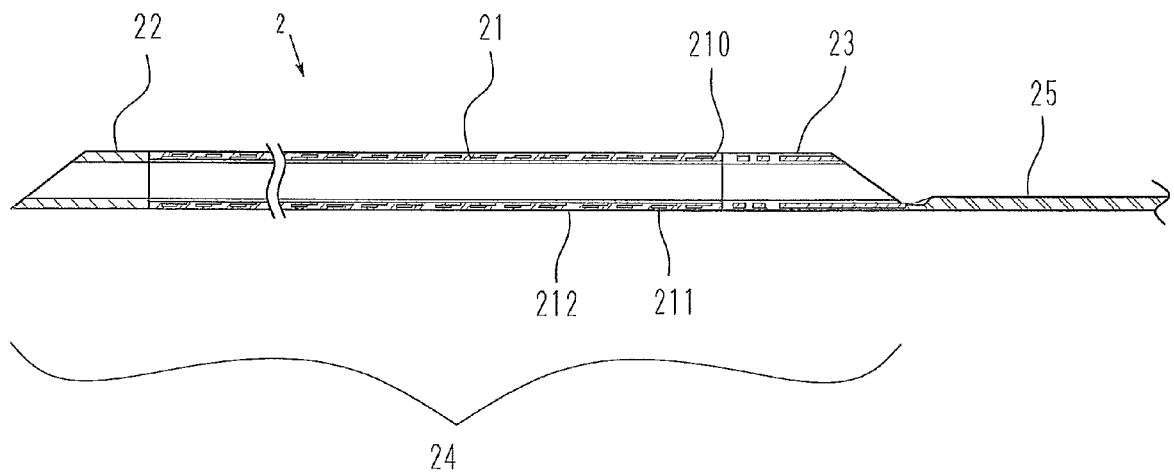
FIG. 3 is a view showing a cross section of a distal end portion of a suction catheter 2.

FIG. 3 shows a sectional view of a distal end portion of the suction catheter 2 of FIG. 1B. Referring to FIG. 3, the suction catheter 2 includes a distal side tubular portion 24, and a proximal side wire-like portion 25 formed from a solid metal wire and an outer layer such as a polymer coating. The tubular portion 24 includes a tubular body portion 21 which in turn includes an inner layer 210 made of a resin material having a sliding property such as a fluorocarbon resin represented by PTFE, a reinforcing layer 211 made of a metal wire made of stainless steel or the like, and an outer layer 212 for covering the reinforcing layer 211, a distal tip 22 provided at the distal end of the tubular body portion 21, and a proximal tip 23 provided at the proximal end of the tubular body portion 21.

The tubular portion 24 has an outer diameter with which the tubular portion 24 can be inserted into the lumen of the guiding catheter 1, and the wire-like portion 25 has a sectional area smaller than the sectional area of the tube wall of the tubular portion 24.

Further, a lubricative coating layer is formed on the surface of the tubular portion 24 by performing hydrophilic lubricative coating which exhibits a high lubricating property when it is wet so that sliding friction of the tubular portion 24 with the inner face of a blood vessel or with the inner surface of the lumen of the guiding catheter 1 is reduced thereby to enhance the insertion feasibility.

The front free end of the distal tip 22 has a shape inclined obliquely with respect to the longitudinal direction of the distal tip 22 to increase the area of the inlet opening thereof thereby to facilitate suction of a foreign matter and further achieve an effect that the distal end of the suction catheter 2 can advance easily between the foreign matter and the inner wall of the blood vessel. Although also the rear end of the proximal tip 23 is similarly inclined obliquely, this is effective to assure the length of the wall for embedding the distal end of the wire-like portion 25 firmly in the proximal tip 23 and assure a large opening area on the proximal end side to enhance the suction force. Since each of the distal tip 22 and the proximal tip 23 is formed such that a filler such as tungsten, bismuth oxide or barium sulfate, which are X-ray contrast agents, is mixed by 50 to 70 wt % in a matrix made of a resin or a matrix made of a metal is plated with gold, it functions as an X-ray contrast marker (radiopaque marker). Consequently, the operator can confirm the positions of the distal end portion of the suction catheter 2 and the proximal end portion of the tubular portion 24 in the body of the patient on an X-ray image.

Figure 4:
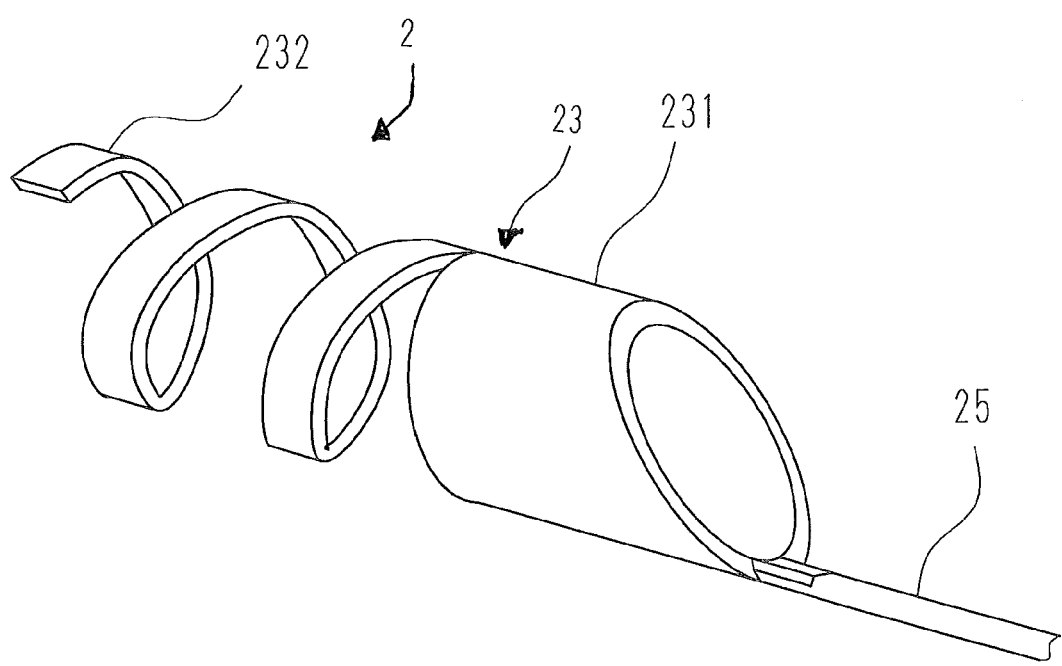
FIG. 4 is a view illustrating a joining method between a tubular portion and a wire-like portion of the suction catheter 2.

FIG. 4 is a view illustrating an example of a method of joining the wire-like portion 25 and the tubular portion 24 together. Referring to FIG. 4, the proximal tip 23 includes a body which in turn includes a proximal end portion 231 formed by obliquely cutting one end of a metal pipe such as a pipe of stainless steel and a distal end portion 232 formed by working the other end portion of the metal pipe into a spiral shape. The inner and outer faces of the body are coated with a resin. The proximal end portion 231 is secured firmly by being welded to the distal end of the wire-like portion 25 crushed into a form of a flat plate so that it may not be broken during use. The resin layers which cover the inner and outer faces of the proximal tip 23 are secured to the tubular body portion 21 by fusion. Where the proximal tip 23 is formed from such a metal material as described above, the surface of the proximal tip 23 is plated with gold. The portion plated with gold functions as an X-ray contrast marker (radiopaque marker).

The distal end protective catheter 5 of FIG. 1E includes a distal end tubular portion 54 which in turn includes a tubular body portion 51, a distal tip 52 provided at the distal end of the tubular body portion 51, a proximal tip 53 provided at the proximal end of the tubular body portion 51, and a proximal end side wire-like portion 55 formed from a metal wire. The distal end protective catheter 5 is inserted in the lumen of the suction catheter 2 and projects from the distal end of the suction catheter 2 such that it acts as a protective safety tip upon insertion into a blood vessel. The distal tip 52 is made of a flexible material and has a thickness greater than that of the distal tip 22 of the suction catheter 2 and has a rounded extremity. The tubular portion 54 and the wire-like portion 55 can be joined together by a method similar to that used for the suction catheter 2 shown in FIG. 4. Also the distal tip 52 and the proximal tip 53 of the distal end protective catheter 5 have a function as a radiopaque marker similarly to those of the suction catheter 2.

The lumen of the tubular body portion 51 of the distal end protective catheter 5 has a size sufficient to receive the guide wire 6 of FIG. 1F therein.

Figure 5:
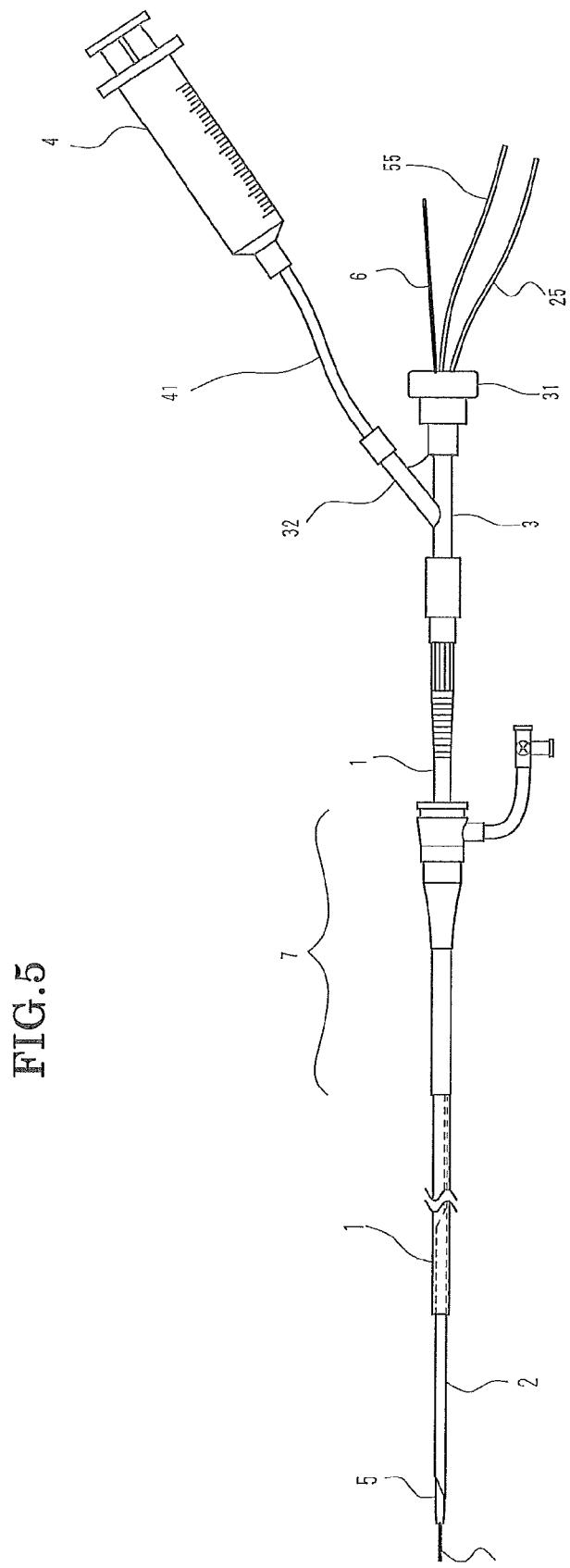
FIG. 5 is a view showing the devices shown in FIG. 1 which are in an assembled state.

FIG. 5 shows the devices and so forth shown in FIG. 1 in a state wherein they are assembled for use. In the present embodiment, the intravascular foreign matter suction assembly is inserted into a blood vessel in a state illustrated in FIG. 5. Referring to FIG. 5, reference numeral 7 denotes an introducer sheath. The introducer sheath 7 is usually used upon ordinary catheter operation, and the introducer sheath 7 is disposed in such a form that it extends from the skin to the inside of a blood vessel thereby to form a path which interconnects the outside of the body and the inside of the blood vessel. Then, catheters are inserted into and used while in the introducer sheath 7. Consequently, the burden on the patient such as pain which is caused by a device slidably moving on a damaged portion of the living organism can be reduced.

Referring to FIG. 5, the Y-shaped connector 3 of FIG. 1C is connected to the connector 13 of the guiding catheter 1; the suction catheter 2 is disposed in the lumen of the guiding catheter 1; the distal end of the distal end protective catheter 5 is inserted in the lumen of the suction catheter 2; and the guide wire 6 is inserted in the lumen of the distal end protective catheter 5. The respective proximal ends of the suction catheter 2, the distal end protective catheter 5, and the guide wire 6 are introduced to the outside through a main connector portion 31 of the Y-shaped connector 3. A valve (packing) which can close up a bore is built in the main connector portion 31 and can selectively clamp and fix the guide wire 6, the wire-like portion 25 or 55 to prevent leakage of the blood. The syringe 4 is connected to a sub connector portion 32 of the Y-shaped connector 3 through a tube 41.

Figure 6:
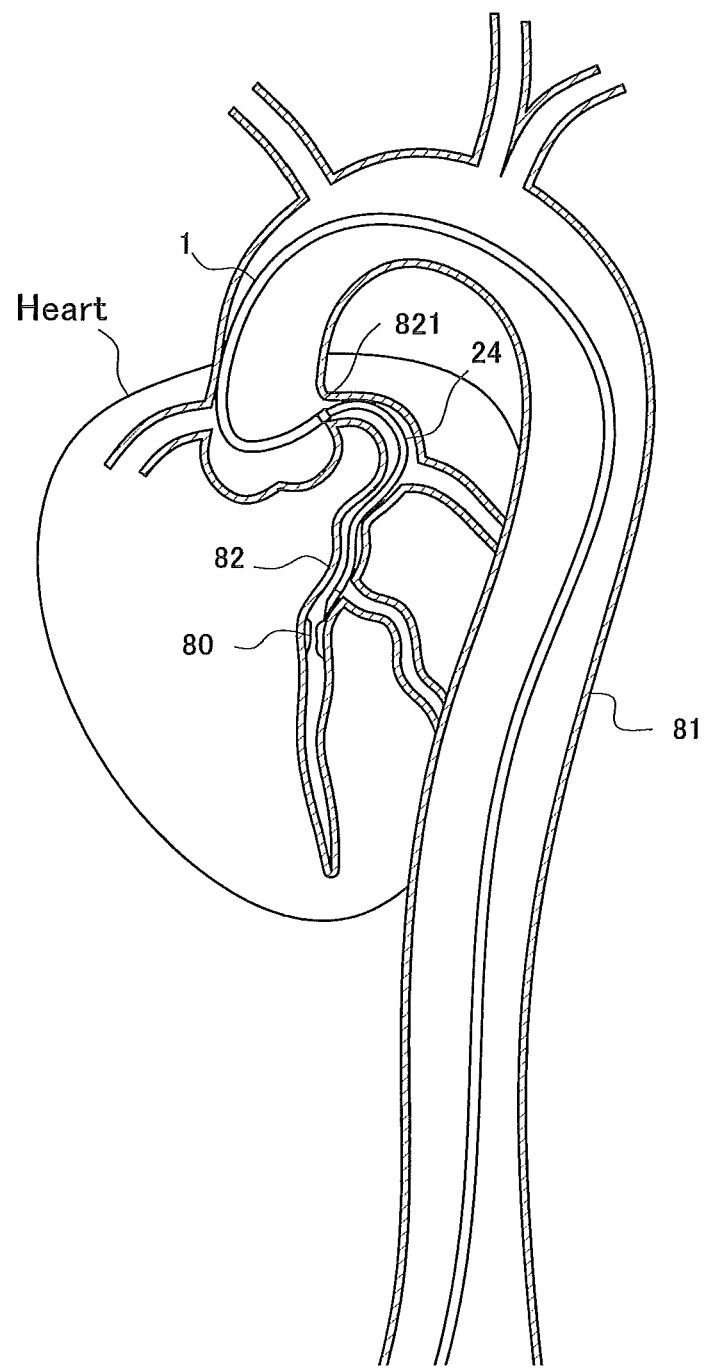
FIG. 6 illustrates a manner wherein the apparatus of the embodiment is disposed at a target location which is in a coronary artery of the heart.

FIG. 6 illustrates a manner of locating the assembly of the present embodiment is at a target location 80 in a coronary artery of the heart.

Referring to FIG. 6, since the guiding catheter 1 is disposed in the aorta 81 of a comparatively great diameter, it can be formed such that each of the inner and outer diameters of the guiding catheter 1 has a comparatively great dimension. The distal end of the guiding catheter 1 is secured in such a form that it is hooked at an ostium 821 of a coronary artery 82.

The tubular portion 24 of the suction catheter 2 has an outer diameter with which it can be inserted into the coronary artery 82 and is introduced along the guide wire 6 to the target location 80 positioned at a deep location. The tubular portion 24 is designed so as to have a sufficient axial length so that the proximal end of the tubular portion 24 in an open state may not leap out from the distal end of the guiding catheter 1 upon such introduction of the tubular portion 24.

The introduction of the suction catheter 2 and the distal end protective catheter 5 to the deep location is performed by pushing in the wire-like portions 25 and 55 on the proximal end side. Accordingly, the sum total of the lengths in the axial direction of the wire-like portion 25 and the tubular portion 24 and the sum total of the length in the axial direction of the wire-like portion 55 and the tubular portion 54 are designed longer by 50 mm or more than the length of the guiding catheter 1 in the axial direction. If the tubular portion 24 is excessively long, then the suction force decreases, and if the wire-like portion 25 is excessively long, then there is the possibility that the proximal end opening of the tubular portion 24 may project from the distal end of the guiding catheter 1. Therefore, it is not preferable that the sum total of the lengths in the axial direction of the wire-like portion 25 and the tubular portion 24 exceeds the length of the guiding catheter 1 in the axial direction by more than 400 mm. Accordingly, it is preferable for the total length of the tubular portion 24 and the wire-like portion 25 of the suction catheter 2 to be greater than the length of the guiding catheter 1 by at least 50 mm but no more than 400 mm.

The devices mentioned have the following dimensions. The guiding catheter 1 preferably has dimensions equal to those of a guiding catheter used in ordinary catheter operation. As a standard length of a guiding catheter used normally, the total length is approximately 1,000 mm. In the following, dimensions of the devices where the length of the guiding catheter 1 is 1,000 mm are given. If the length of the guiding category changes, then also the lengthwise dimensions of the wire-like portions of the devices are preferably changed similarly.

Preferably, the length of the tubular portion 24 of the suction catheter 2 is a little greater than a length with which the tubular portion 24 can reach a coronary artery of the heart and particularly is 100 mm to 200 mm. Where the length of the tubular portion 24 is smaller than 100 mm, depending upon the target location, the distal end of the tubular portion 24 cannot sometimes reach the target location, but where the length of the tubular portion 24 is greater than 200 mm, there is the possibility that a preferable suction force may not be obtained. Preferably, the length of the wire-like portion 25 of the suction catheter 2 ranges from 950 mm to 1,200 mm. If the length of the wire-like portion 25 is smaller than 950 mm, then the tubular portion 24 at the distal end of the wire-like portion 25 cannot be extended sufficiently. On the other hand, if the length of the wire-like portion 25 is greater than 1,200 mm, then there is the possibility that the proximal end opening of the tubular portion 24 may project from the distal end of the guiding catheter 1. If the proximal end opening of the tubular portion 24 were to project from the distal end of the guiding catheter 1, then upon suction, the blood would be sucked not at the distal end of the suction catheter 2 but at the distal end of the guiding catheter 1. It is to be noted that the proximal tip 23 provided at the proximal end of the tubular portion 24 has a function of a radiopaque marker, the operator can observe an X-ray image to confirm so that the proximal tip 23 of the suction catheter 2 may not advance farther than the distal end of the guiding catheter 1.

The length of the tubular portion 54 of the distal end protective catheter 5 preferably ranges from 20 mm to 50 mm. If the length of the tubular portion 54 were smaller than 20 mm, then the effect of protecting the distal end of the suction catheter 2 when the suction catheter 2 is advanced would not be achieved sufficiently. However, if the length of the tubular portion 54 were longer than 50 mm, then the flexibility of the distal end portion thereof would be insufficient when the tubular portion 54 is combined with the suction catheter 2 to such a degree that it could not be introduced well into a winding blood vessel.

The preferred devices have the following diameters. In particular, the guiding catheter 1 is formed from a guiding catheter of 6 Fr (2.06 mm) which is used popularly and has an inner diameter of 1.8 mm. The outer diameter of the suction catheter 2 preferably is within a range from 1.65 mm to 1.75 mm. In particular, the difference between the inner diameter of the guiding catheter 1 and the outer diameter of the suction catheter 2 preferably is within a range from 0.05 mm to 0.15 mm. If the difference is smaller than 0.05 mm, then the passing performance (sliding performance) of the guiding catheter 1 in the suction catheter 2 is low and the convenience in use is poor. On the other hand, if the difference is greater than 0.15 mm, then when a sucking operation is performed by the syringe 4, the blood is sucked in through the gap (clearance) between the distal end of the guiding catheter 1 and the suction catheter 2, which causes the suction performance from the distal end of the suction catheter 2 to deteriorate. It is to be noted that, since a lubricative coating layer is provided on the surface of the tubular body portion 21 of the suction catheter 2, even when the clearance is small, the suction catheter 2 can move smoothly in the guiding catheter 1.

An example of a method of use of the intravascular foreign matter suction assembly of the present embodiment is described below.

(1) The introducer sheath 7 is inserted into and disposed in the aorta of a femoral region by an ordinary method (e.g., the Seldinger method).

(2) The guiding catheter 1 to which the Y-shaped connector 3 to which the syringe 4 is attached is connected and which has the guide wire 6 fitted therein is inserted into the introducer sheath 7 and secured to the ostium of a coronary artery.

(3) The guide wire 6 is inserted to a target location while an X-ray image is observed.

(4) A combination of the suction catheter 2 and the distal end protective catheter 5 is inserted into the guiding catheter 1 along the guide wire 6.

(5) The distal end of the combination of the suction catheter 2 and the distal end protective catheter 5 is inserted to the target location 80.

(6) The distal end protective catheter 5 is pulled out.

(7) The suction catheter 2 is operated so as to be rotated, pushed or pulled until the distal end opening thereof is introduced to a location in front of a thrombus 80 as seen in FIG. 6.

(8) The syringe 4 is operated for suction to recover foreign matters in the blood vessel such as the thrombus through the distal end of the suction catheter 2.

Figure 7B:
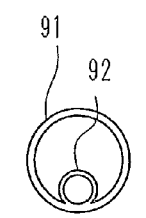
FIG. 7B is a front end view of FIG. 7A.
Figure 7A:
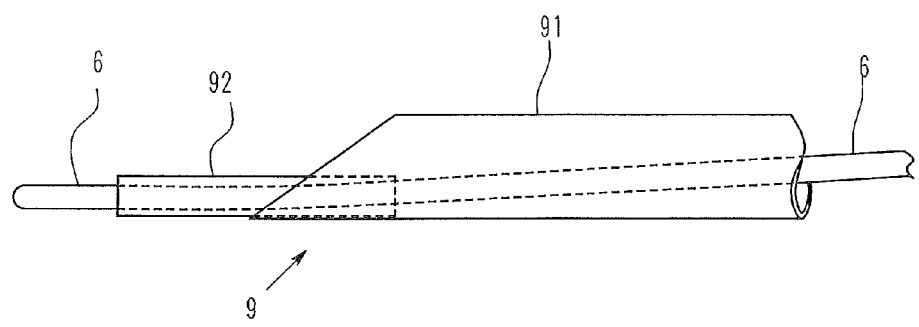
FIG. 7A is a side view showing a modification to a suction catheter.
Figure 8:
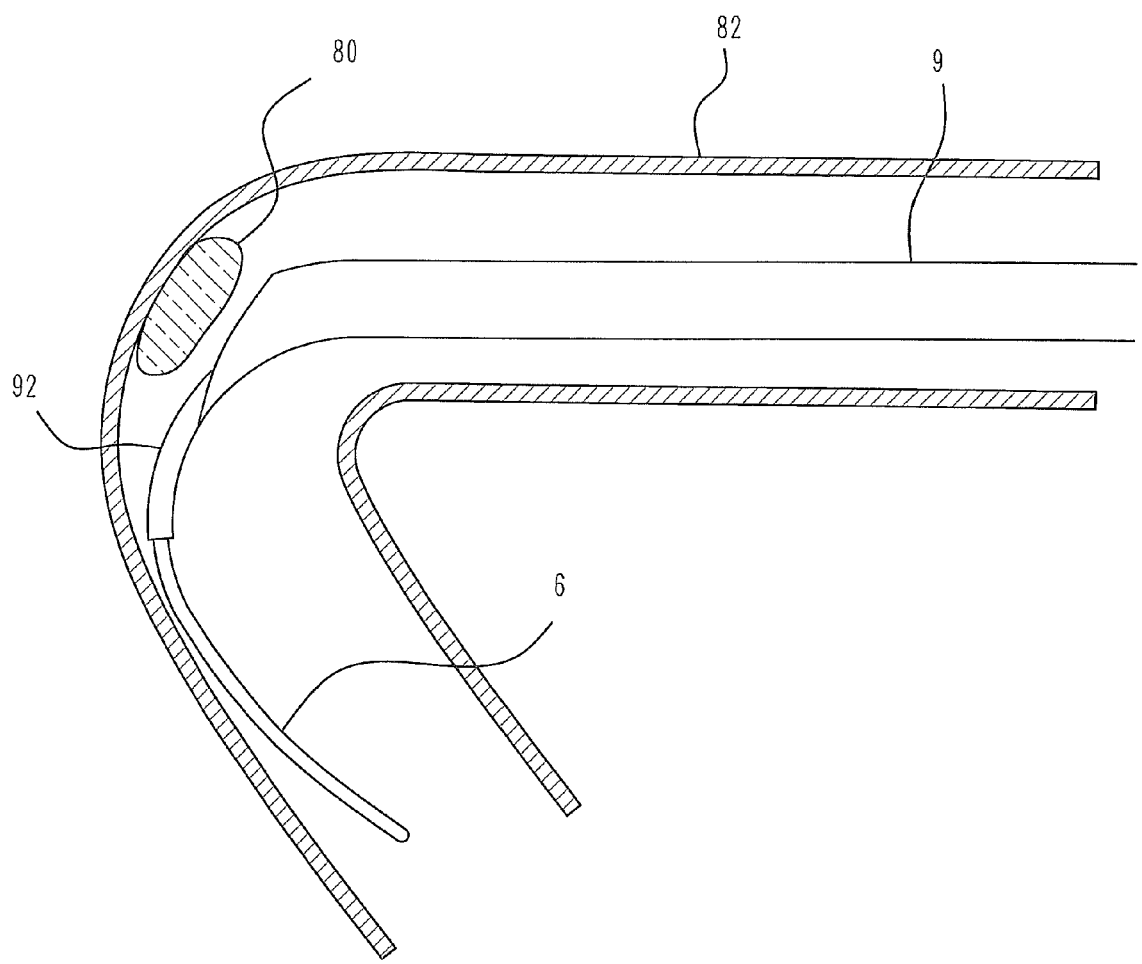
FIG. 8 is a view illustrating a manner of removal of a thrombus by the modification.

Modification:

FIGS. 7A-7B are views showing a modification of the suction catheter of the embodiment described above. In the suction catheter 9 shown in those figures, a guide wire lumen tube 92 having a small diameter is secured to the distal end of a tubular portion 91. It is to be noted that a proximal end side wire-like portion not shown of the suction catheter 9 has the same structure as that of the embodiment described hereinabove. According to the present modification, since the follow-up performance of the suction catheter 9 along the guide wire 6 is enhanced, where the diseased part is positioned in a blood vessel having a severe winding or at a portion near to the periphery, the opening can be directed to a thrombus 80 as seen in FIG. 8 and can suck and remove the thrombus 80 efficiently. Further, the necessity for the distal end protective catheter 5 is eliminated.

The outer diameter of the guide wire lumen tube 92 is smaller than one half the inner diameter of the tubular portion 91 so that the guide wire lumen tube 92 may not make an obstacle to the suction.

Example

An intravascular foreign matter suction assembly of the embodiment described above having dimensions specified in Table 1 below was fabricated.

TABLE 1

| Name of device | Overall length (mm) | Outer diameter (mm) | Inner diameter (mm) |
|---|---|---|---|
| Guiding catheter 1 | 1000 | 2.06 | 1.8 |
| Suction catheter 2 (tubular portion) | 150 | 1.72 | 1.5 |
| Suction catheter 2 (wire-like portion) | 1100 | 0.45 | — |
| Distal end protective catheter 5 (tubular portion) | 20 | 1.35 | 0.5 |
| Distal end protective catheter 5 (wire-like portion) | 1300 | 0.45 | — |

(Comparative Experiment)

Figure 9A:
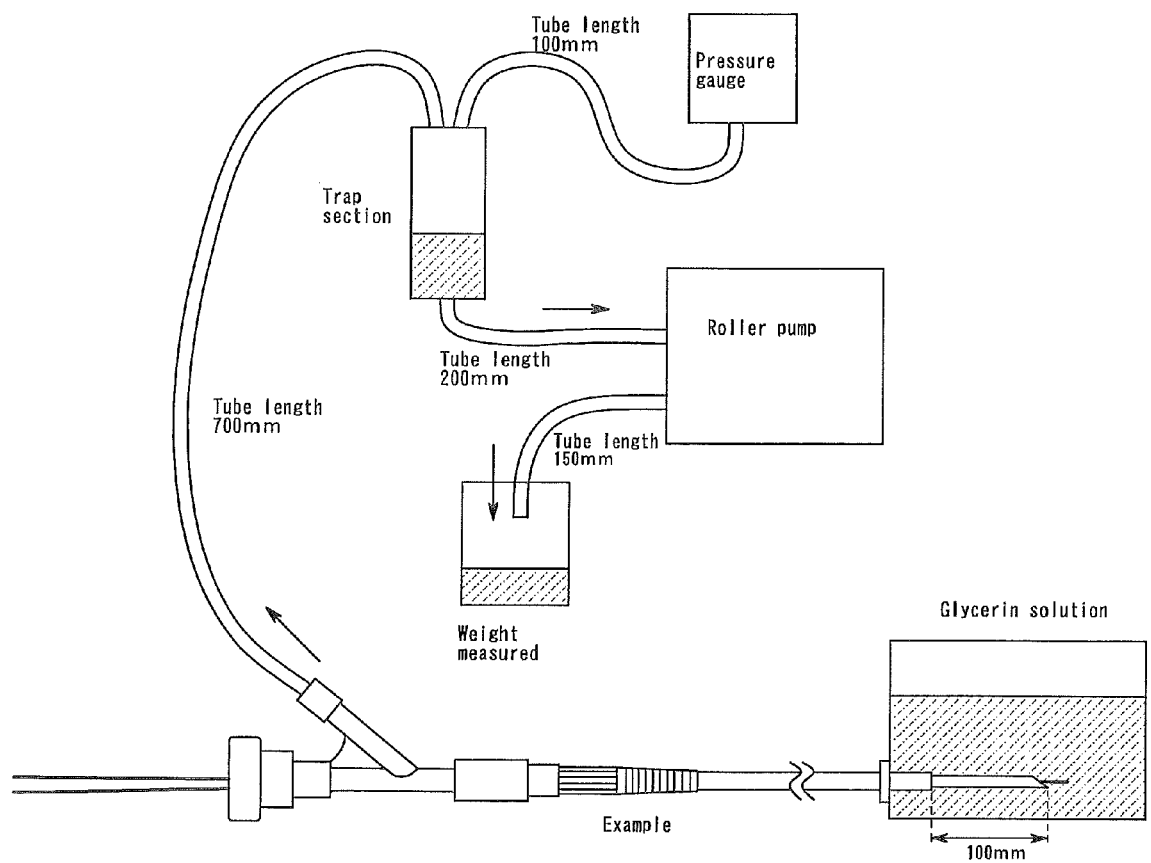
Figure 9B:
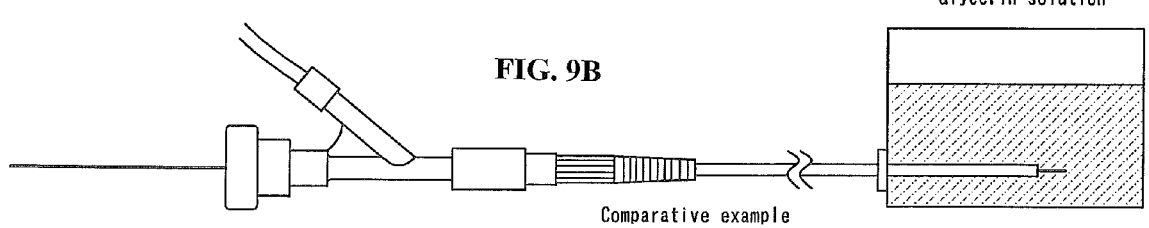
Figure 10:
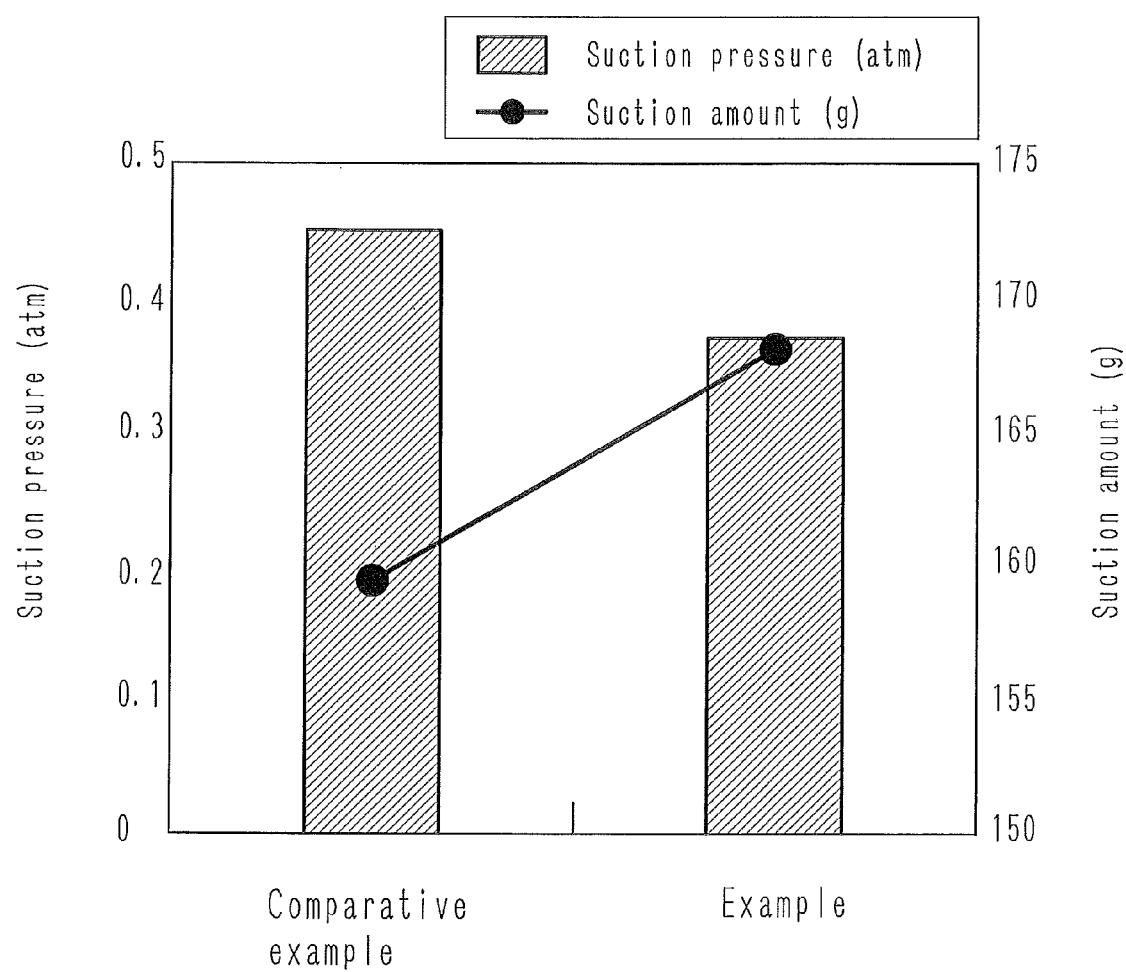
FIG. 10 is a view illustrating a result of the comparative experiment.

A comparative experiment of the suction force was conducted in a configuration shown in FIGS. 9A-9B using the intravascular foreign matter suction assembly of the example and a straight catheter (total length of 1,100 mm) having a tubular form along the overall length thereof and having inner and outer diameters equal to those of the tubular portion of the suction catheter used in the apparatus of the example.

For the experiment, a method was used wherein the distal end of the catheter was received in a water tank in which glycerin solution of a concentration of 47 wt % was filled, and in a state wherein the guide wire was threaded, the glycerin solution was sucked at a rate of 100 ml/min by means of a roller pump which was on the market. The weight of the liquid obtained by the suction for 2 minutes and the maximum negative pressure recorded within the period were measured.

The projecting length of the distal end of the suction catheter of the example from the guiding catheter was 100 mm. Accordingly, the effective sectional area used for the suction was 1.6 mm$^2$ at the distance of 150 mm on the distal end side and 2.1 mm$^2$ at the distance of 950 mm on the proximal end side (the effective sectional area is given as a value except for the sectional area (0.2 mm$^2$×2) of the guide wire 6 and the catheter wire-like portion 25 of the suction catheter 2).

As a comparative example, a straight catheter having an outer diameter of 1.72 mm, an inner diameter of 1.5 mm and an overall length of 1,100 mm which are equal to the dimensions of the tubular portion of the suction catheter of the example was used. Accordingly, the effective sectional area is 1.6 mm$^2$ over the overall length (the effective sectional area is given as a value except for the sectional area (0.2 mm$^2$) of the guide wire 6.)

The roller pump serving as a suction apparatus, a pressure gauge and so forth other than the catheters were used commonly to the example and the comparative example.

While an embodiment of the present invention is described above, the present invention is not limited to the embodiment described above. For example, a syringe presented as the negative pressure generation means can be replaced by a pump.

What is claimed is:

1. A method of sucking foreign matter from a blood vessel, comprising:
    inserting into a blood vessel a guiding catheter until a distal side of the guiding catheter reaches a proximal side of a target location;
    simultaneously moving a suction catheter and a protective catheter within a lumen of the guiding catheter, the suction catheter comprising a tubular portion and a solid wire portion extending from a proximal side of the tubular portion, towards a position in which a distal side of the tubular portion projects forwardly beyond the distal side of the guiding catheter, and a proximal side of the tubular portion is disposed inside of the guiding catheter;

withdrawing the protective catheter from the suction catheter;

rotating the suction catheter until a distal end of the suction catheter is introduced to a location in front of a thrombus; and applying suction to the guiding catheter which is transmitted to the tubular portion for sucking the foreign matter into the distal side of the tubular portion.

2. The method according to claim 1, wherein the suction is applied to the guiding catheter by activating a negative pressure generating device connected to a proximal end of the guiding catheter.

3. The method according to claim 2, wherein, when the negative pressure generating device generates a negative pressure, the foreign matter is substantially sucked only through an opening at a distal end of the suction catheter and is not substantially sucked through a distal end of the guiding catheter.

4. The method according to claim 1, wherein the guiding catheter has a minimum inner diameter greater than a maximum outer diameter of the suction catheter by at least 0.05 mm and no more than 0.15 mm.

5. The method according to claim 1, wherein the total length of the tubular portion and the solid wire portion of the suction catheter is greater than that of the guiding catheter by a length which is at least 50 mm but no more than 400 mm.

6. The method according to claim 1, wherein a distal end of the suction catheter has an obliquely cut shape.

7. The method according to claim 1, wherein the suction catheter has a radiopaque marker in a vicinity of the proximal side of the tubular portion.

8. The method according to claim 1, wherein the guiding catheter has a radiopaque marker in a vicinity of its distal side.

9. The method according to claim 1, wherein an outer surface of the tubular portion of the suction catheter has a lubricative coating.

10. A method of sucking foreign matter from a blood vessel, comprising:

inserting into a blood vessel a guiding catheter until a distal side of the guiding catheter reaches a proximal side of a target location;

simultaneously moving a suction catheter and a protective catheter within a lumen of the guiding catheter, the suction catheter comprising a tubular portion, towards a position in which a distal side of the tubular portion projects forwardly beyond the distal side of the guiding catheter, and a proximal side of the tubular portion is disposed inside of the guiding catheter;

withdrawing the protective catheter from the suction catheter;

rotating the suction catheter until a distal end of the suction catheter is introduced to a location in front of a thrombus; and applying suction to the tubular portion for sucking the foreign matter into the distal side of the tubular portion.

11. The method according to claim 10, wherein the suction is applied to the tubular portion by activating a negative pressure generating device connected to a proximal end of the guiding catheter.

12. The method according to claim 11, wherein, when the negative pressure generating device generates a negative pressure, the foreign matter is substantially sucked only through an opening at a distal end of the suction catheter and is not substantially sucked through a distal end of the guiding catheter.

13. The method according to claim 10, wherein the guiding catheter has a minimum inner diameter greater than a maximum outer diameter of the suction catheter by at least 0.05 mm and no more than 0.15 mm.

14. The method according to claim 10, wherein a distal end of the suction catheter has an obliquely cut shape.

15. The method according to claim 10, wherein the suction catheter has a radiopaque marker in a vicinity of the proximal side of the tubular portion.

16. The method according to claim 10, wherein the guiding catheter has a radiopaque marker in a vicinity of its distal side.

17. The method according to claim 10, wherein an outer surface of the tubular portion of the suction catheter has a lubricative coating.

18. A method of sucking foreign matter from a blood vessel, comprising:

inserting into a blood vessel a guiding catheter until a distal side of the guiding catheter reaches a proximal side of a target location;

simultaneously moving a suction catheter and a protective catheter within a lumen of the guiding catheter, the suction catheter comprising a tubular portion, towards a position in which a distal side of the tubular portion projects forwardly beyond the distal side of the guiding catheter, and a proximal side of the tubular portion is disposed inside of the guiding catheter;

withdrawing the protective catheter from the suction catheter; and applying suction to the tubular portion for sucking the foreign matter into the distal side of the tubular portion, wherein the guiding catheter has a minimum inner diameter greater than a maximum outer diameter of the suction catheter by at least 0.05 mm and no more than 0.15 mm, the suction is applied to the tubular portion by activating a negative pressure generating device connected to a proximal end of the guiding catheter, and when the negative pressure generating device generates a negative pressure, the foreign matter is substantially sucked only through an opening at a distal end of the suction catheter and is not substantially sucked through a distal end of the guiding catheter.

19. The method according to claim 18, further comprising rotating the suction catheter until the distal end of the suction catheter is introduced to a location in front of a thrombus.

20. The method according to claim 18, wherein the suction catheter further comprises a solid wire portion extending from the proximal side of the tubular portion.

* * * * *